(12) United States Patent
Drueding et al.

(10) Patent No.: US 9,885,623 B2
(45) Date of Patent: Feb. 6, 2018

(54) METHOD AND SYSTEM FOR SIMULTANEOUSLY STARTING ACTIONS OF DEVICES

(71) Applicant: Advanced Mechanical Technology, Inc., Watertown, MA (US)

(72) Inventors: Albert C. Drueding, Belmont, MA (US); Gary M. Glass, Newton, MA (US)

(73) Assignee: Advanced Mechanical Technology, Inc., Watertown, MA (US)

( * ) Notice: Subject to any disclaimer, the term of this patent is extended or adjusted under 35 U.S.C. 154(b) by 0 days.

(21) Appl. No.: 15/010,102

(22) Filed: Jan. 29, 2016

(65) Prior Publication Data

US 2016/0252416 A1    Sep. 1, 2016

Related U.S. Application Data

(62) Division of application No. 13/273,864, filed on Oct. 14, 2011, now Pat. No. 9,255,859.

(Continued)

(51) Int. Cl.
*G01L 25/00* (2006.01)
*G01L 5/16* (2006.01)
(Continued)

(52) U.S. Cl.
CPC ............. *G01L 5/16* (2013.01); *A61B 5/1036* (2013.01); *A61B 5/1038* (2013.01); *A61B 5/112* (2013.01);
(Continued)

(58) Field of Classification Search
CPC .................................. G01L 25/00; G01L 5/16
See application file for complete search history.

(56) References Cited

U.S. PATENT DOCUMENTS 4,493,220 A    1/1985  Carignan et al.
4,799,559 A    1/1989  Murder
(Continued)

OTHER PUBLICATIONS

"Relay Judging Platform: Lighted and Standard versions," Web page <http://www.coloradotime.com/pdf/Relayo/o20Judgingo/o20Piatform.pdf>, 2 pages, dated Sep. 9, 2009, retrieved from Internet Archive Wayback Machine on Jun. 6, 2014 (URL on Evid. Publ).

(Continued)

*Primary Examiner* — Bryan Bui
(74) *Attorney, Agent, or Firm* — Hamilton, Brook, Smith & Reynolds, P.C.

(57) ABSTRACT

A method of processing force signals from plural force platforms includes, in a computer, in an initialization process, receiving data distinguishing the plural platforms, monitoring force data signals from each of the plural platforms, and identifying each of the plural platforms to a force platform data process application by a sequence of received above-threshold force data signals. The method further includes, subsequent to the initialization process, processing subsequent force data signals according to the identification of each of the plural force platforms. The distinguishing data can include data retrieved from nonvolatile memory of each of the plural force platforms, such as a platform serial number, calibration data, and force platform capacity. A force platform system includes one or more force platforms and force platform signal conditioning circuitry connected to the one or more force platforms. The signal conditioning circuitry may include a separate signal conditioner connected to each force platform.

12 Claims, 10 Drawing Sheets

Related U.S. Application Data

(60) Provisional application No. 61/413,881, filed on Nov. 15, 2010.

(51) Int. Cl.
*A61B 5/00* (2006.01)
*A61B 5/103* (2006.01)
*A61B 5/11* (2006.01)
*G01G 19/44* (2006.01)
*G01G 21/23* (2006.01)

(52) U.S. Cl.
CPC .......... *A61B 5/4023* (2013.01); *A61B 5/6887* (2013.01); *A61B 5/7235* (2013.01); *G01L 5/161* (2013.01); *G01L 25/00* (2013.01); *A61B 5/1116* (2013.01); *A61B 2560/0223* (2013.01); *A61B 2562/0247* (2013.01); *G01G 19/44* (2013.01); *G01G 21/23* (2013.01)

(56) References Cited

U.S. PATENT DOCUMENTS

| | | | |
|---|---|---|---|
| 5,400,661 | A | 3/1995 | Cook et al. |
| 5,606,516 | A | 2/1997 | Douglas |
| 5,623,944 | A | 4/1997 | Nashner |
| 5,814,740 | A | 9/1998 | Cook et al. |
| 6,402,635 | B1 | 6/2002 | Nesbit et al. |
| 6,525,658 | B2 | 2/2003 | Streetman et al. |
| 9,255,859 | B2 | 2/2016 | Drueding et al. |
| 2004/0148539 | A1* | 7/2004 | Leydier ............... G06F 1/04 713/500 |
| 2007/0078488 | A1 | 4/2007 | Bjorling et al. |
| 2009/0222685 | A1 | 9/2009 | Foster et al. |
| 2010/0004876 | A1 | 1/2010 | Loher et al. |
| 2012/0035869 | A1 | 2/2012 | Lin et al. |

OTHER PUBLICATIONS

0R6-6 Force Platform (Advanced Mechanical Technology, Inc.), date unknown, (2 pages).

AMTI introduces the next generation in strain gage amplifiers . . . Gen 5: Advanced six-channel signal conditioner (Advanced Mechanical Technology, Inc.), Retrieved from Internet URL: http://amti.biz/gen5.pdf (2 pages).

Bertec Force Plate Product Description from www.bertec.com, pp. 1-2, publicly available on or before Jan. 8, 2005.

GEN 5: Advanced six-channel signal conditioner (Advanced Mechanical Technology, Inc.) [online], date unknown [Retrieved on Oct. 17, 2011], Retrieved from Internet URL: http://amti.biz/gen5.aspx.

Leu, Ching-Shan, "A Z-808 Based Data Acquisition System as a Smart Interface Between the Modular Force Plate and PDP-11/34 Minicomputer", cover page, pp. 1-11 and 13-50, publicly available on Feb. 8, 1985.

OR6-6-1000 Specification (Advanced Mechanical Technology, Inc.), [online] Last modified Oct. 22, 2010 [Retrieved on Nov. 2, 2010], Retrieved from Internet URL: http://www.amti.biz/AMTIpibrowser.aspx?_VIEWSTATE=%2FwEPDwULLTE0NzQ1NDQ3OTNkZA%3D%3D&iListbox1=350&iListbox2=375&iListbox3=OR6-GT&iUnits=&iNewpageURL=&iScrollTop=0&iScrollTop2=127&iScrollTop3=0 Also available at: http://tinyurl.com/822ulfz.

Universal Serial Bus (USB) Specification—Revision 2.0, pp. i-ii and 71-83, publicly available on www.usb.org on or before Dec. 22, 2002.

Marco Benocci, et al., "A Wireless System for Gait and Posture Analysis Based on Pressure Insoles and Inertial Measurement Units", published in Pervasive Computing Technologies for Healthcare, 2009; Conference Date: Apr. 1-3, 2006; pp. 1-6.

\* cited by examiner

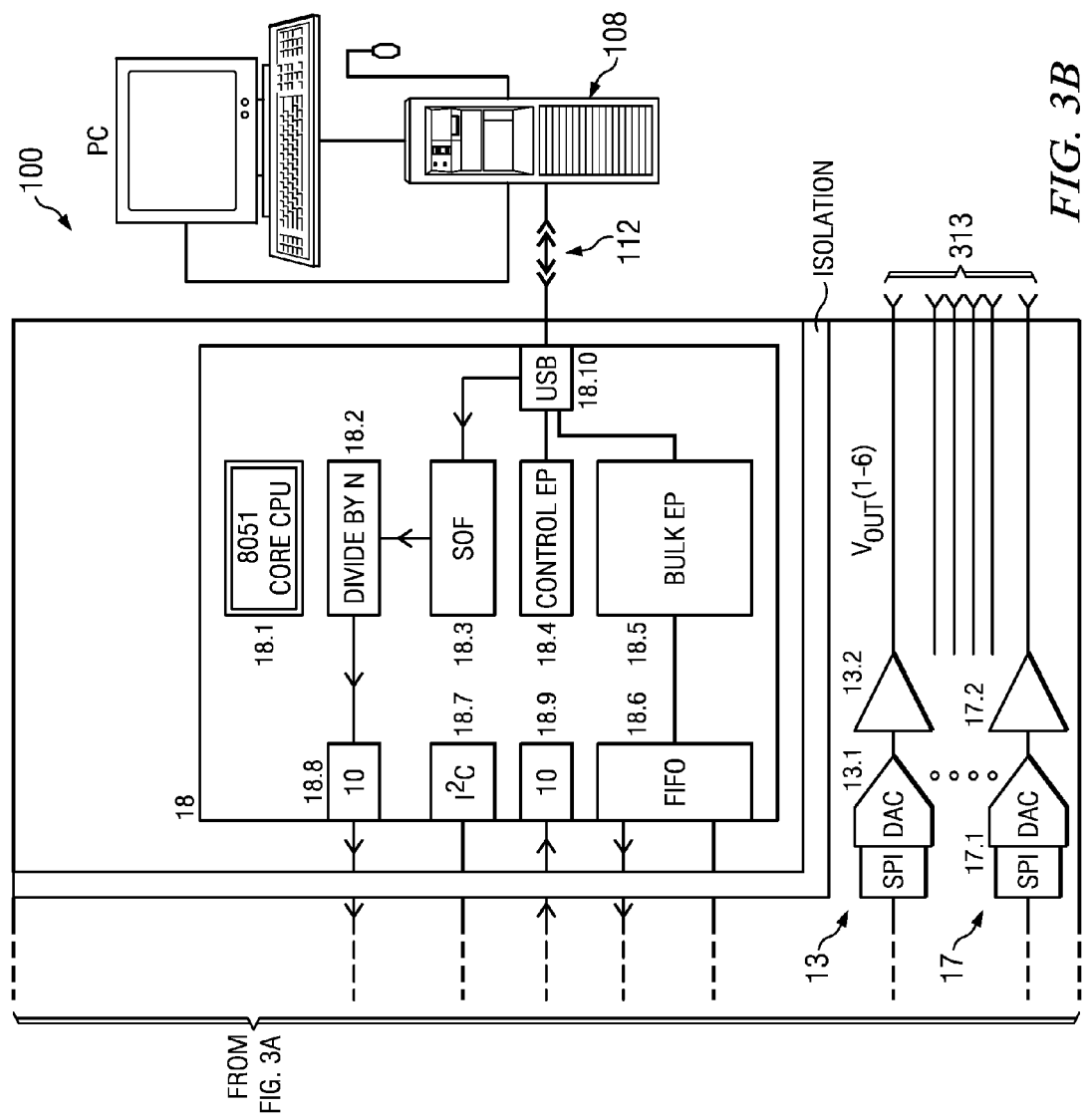

METHOD AND SYSTEM FOR SIMULTANEOUSLY STARTING ACTIONS OF DEVICES

RELATED APPLICATIONS

This application is a divisional of U.S. application Ser. No. 13/273,864, filed Oct. 14, 2011, which claims the benefit of U.S. Provisional Application No. 61/413,881, filed on Nov. 15, 2010.

The entire teachings of the above applications are incorporated herein by reference.

BACKGROUND OF THE INVENTION

In the field of Biomechanics, force platforms are used to study human gait and balance. A force platform is a measuring device that measures ground reaction forces. Typically force platforms are mounted in a pit so that their top surface lies flush with the floor. Subjects are then instructed to walk across or stand on the platforms and the generated ground reaction forces are recorded. For many gait studies multiple force platforms are required to capture ground reaction forces of one or more strides of a person's gait cycle.

A system used to measure ground reaction forces consists of several components. The individual components are typically a force plate, an amplifier or signal conditioner, either connected to or embedded in the force plate or platform, and a computer for data collection. Data collection can be either digital or analog depending on the medium chosen. In addition, both the force plate and the signal conditioner require calibration to accurately convert raw data to usable data.

SUMMARY OF THE INVENTION

A method of processing force signals from plural force platforms includes, in a computer in an initialization process, receiving data distinguishing the plural force platforms, monitoring force data signals from each of the plural force platforms, and identifying each of the plural platforms to a force platform data process application by a sequence of received above-threshold force data signals. The method also includes, subsequent to the initialization process, processing subsequent force data signals according to the identification of each of the plural force platforms.

The distinguishing data may include data received from nonvolatile memory of each of the plural force platforms, such as a force platform serial number, calibration data, and/or force platform capacity.

A system for processing force signals from plural force platforms includes a computer configured to, in an initialization process, receive data distinguishing the plural force platforms, monitor force data signals from each of the plural force platforms, and identify each of the plural force platforms to a force platform data process application by a sequence of received above-threshold force data signals. The computer is further configured to, subsequent to the initialization process, process subsequent force data signals according to the identification of each of the plural force platforms.

A computer program product includes a non-transitory computer readable medium having computer-executable instructions stored thereon, which, when loaded and executed by a processor, cause the processor to, in an initialization process, receive data distinguishing plural force platforms, monitor force data signals from each of the plural force platforms, and identify each of the plural force platforms to a force platform data process application by a sequence of received above-threshold force data signals. Also included are instructions which cause the processor to, subsequent to the initialization process, process subsequent force data signals according to the identification of each of the plural force platforms.

A force platform includes one or more force transducers, an output to output force signals from the one or more force transducers, and nonvolatile memory storing calibration data retrievable by external electronics.

The nonvolatile memory can further store a force platform serial number retrievable by external electronics, and/or force platform capacity retrievable by the external electronics. The nonvolatile memory can be programmable, including reprogrammable memory, such as an EPROM.

A force platform signal conditioner includes an input configured to receive force signals from a force platform, and electronics configured to retrieve platform calibration data from the force platform and condition the force signals received at the input based on the retrieved platform calibration data. The force platform signal conditioner also includes an output to output the conditioned force signals.

The conditioner electronics can include nonvolatile memory storing conditioner calibration data, in which case the electronics may condition the force signals based on the platform calibration data and the conditioner calibration data. Further, the electronics can include an analog to digital converter to convert received analog force signals to digital signals, and the force signals can therefore be conditioned digitally. The output may include a digital output, which can include a Universal Serial Bus (USB) port. Alternatively, or in addition, the electronics can include a digital to analog converter to convert the conditioned force signals to an analog signal output.

The conditioner electronics may be configured to retrieve a serial number from the force platform and communicate the serial number through an output. The electronics may also be configured to retrieve a platform capacity from the force platform and communicate the platform capacity through an output.

A force platform system includes one or more force platforms. Each force platform includes one or more force transducers, a platform output to output force signals from the one or more force transducers, and nonvolatile memory storing calibration data. The force platform system also includes force platform signal conditioning circuitry connected to the force platforms. The signal conditioning circuitry includes an input configured to receive force signals from each connected force platform and a signal conditioner output to output the conditioned force signals. Also included are electronics configured to retrieve platform calibration data from each connected force platform and to condition the force signals received at the input based on the retrieved platform calibration data.

The signal conditioning circuitry may include a separate signal conditioner connected to each force platform. The electronics of the signal conditioning circuitry may further include nonvolatile memory storing signal conditioning calibration data and the electronics may condition the force signals based on the connected platform calibration data and the signal conditioning calibration data. In some embodiments, the electronics of the signal conditioning circuitry further include an analog to digital converter to convert received analog force signals to digital signals and the force signals are conditioned digitally.

A method of simultaneously starting actions of devices connected to a host includes repeatedly transmitting a start of frame signal to the connected devices, the start of frame signal being received by the connected devices at the same time. The method further includes, in the host, determining a starting frame number and issuing a start command to the connected devices, the start command including the determined starting frame number. Further yet, the method includes, in the connected devices, inspecting the received start of frame signal to determine an associated frame number, receiving the start command, and upon receipt of the start command, starting an action of the devices in response to the associated frame number being equal to the determined starting frame number.

In some embodiments, the devices are connected to the host via a USB connection. Issuing a start command may include serially issuing start commands. Each of the start commands may be addressed to one of the connected devices and may include the starting frame number. Further, determining the starting frame number may include determining the associated frame number of the start of frame signal as one that will be transmitted after all serially issued start commands have reached the connected devices. In an embodiment, starting an action of the devices includes starting data acquisition with the devices An electronic device includes electronics configured to repeatedly receive a start of frame signal, inspect the received start of frame signal to determine an associated frame number, and receive a start command that includes a starting frame number. The electronics are also configured to, upon receipt of the start command, start an action of the device in response to the associated frame number being equal to the starting frame number.

A system for simultaneously starting actions of devices includes plural devices connected to a host. The devices include electronics configured to repeatedly receive a start of frame signal, the start of frame signal being received by the connected devices at the same time. The electronics are also configured to inspect the received start of frame signal to determine an associated frame number, and receive a start command issued by the host, the start command including a starting frame number determined by the host. The electronics are further configured to, upon receipt of the start command, start an action of the devices, e.g. data acquisition with the devices, in response to the associated frame number being equal to the starting frame number.

The devices can be connected to the host via a USB connection. The issued start command can include serially issued start commands, each of the start commands being addressed to one of the connected devices and including the starting frame number. In the case of serially issued start commands, the host may determine the starting frame number by determining the associated frame number of the start of frame signal as one that will be transmitted after all serially issued start commands have reached the connected devices.

A method of timing data sampling includes, in a data acquisition device, generating sampling intervals from a system clock, sampling data at the generated sampling intervals, and receiving start of frame signals from a port. Further, the method includes, for a selected number of start of frame signals received, determining an actual number of system clock cycles for a time interval corresponding to the selected number of start of frame signals, comparing the actual number of system clock cycles to a nominal number of system clock cycles, and adjusting a sampling interval based on the comparison.

In some embodiments, determining the actual number of system clock cycles or ticks includes using a count-and-capture counter. The nominal number of system clock cycles or ticks may be calculated based on a nominal system clock rate and on a known start of frame interval. In some embodiments, generating sampling intervals comprises using a divide-by-N counter. The port from which start of frame signals are received may be a USB port.

A data acquisition device includes an interval generator that generates sampling intervals from a system clock, a data sampler that samples data at the generated sampling intervals, and an input port that receives start of frame signals from a port, such as a USB port. Also included is a sampling interval adjuster configured to determine an actual number of system clock cycles for a time interval corresponding to a selected number of start of frame signals. The adjuster is further configured to compare the actual number of system clock cycles to a nominal number of system clock cycles and adjust the length of the sampling intervals based on the comparison.

The sampling interval adjuster may include a count-and-capture counter, and the actual number of system clock cycles can be determined using the count-and-capture counter. The nominal number of system clock cycles may be calculated based on a nominal system clock rate and a known start of frame interval. The interval generator may include a divide-by-N counter, and the sampling intervals can be generated using the divide-by-N counter.

A force platform system according to the principles of the present invention has many advantages. For example, the force platform system provides an efficient way to define the geometrical organization of the platforms and the organization of the data. In addition, the force platform system facilitates organizing and coordinating the individual components of a single or multi-platform system allowing for easy setup, configuration, and reconfiguration as the testing environment changes. In conventional force platform systems, calibration is often done manually and separately for each component of the system. This places a burden on the user to record the calibration data. For multiple force platform systems, this burden is increased because the user must associate the correct calibration data with each of the various components in the system. Furthermore, many prior force platform systems include an analog card using analog inputs connected using multiple wires, which make it difficult and time consuming to reconfigure such systems.

A benefit of the force platform according present invention is the nonvolatile memory that can store platform calibration and/or identification data that are retrievable by external electronics. In this way, a signal conditioner, for example, can retrieve and apply the correct calibration parameters in a manner that is transparent to the user. In addition, the relationship between the configuration of the physical layout of multiple platforms and the data storage format may be easily definable and implemented in a manner that is transparent to the user. For example, a designated platform order may be set by having a subject traverse the platforms in the desired sequence. Another benefit is the ability of the signal conditioner to utilize a novel scheme for synchronizing digital data acquisition across multiple USB data acquisition devices, e.g., multiple signal conditioners connected to a host computer, via existing signals on the USB. In this way, data from all force platforms connected to the signal conditioners can be synchronized in time without the need for additional wiring. These and other features described herein decrease set-up time, increase flexibility in configuring the system, and decrease risk of user error as compared to conventional force platform systems.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3A and FIG. 3B together are a diagram of the hardware architecture of a force platform system including a signal conditioner, a force platform, and a PC according to an embodiment of the invention. FIG. 3 shows the relationship between FIG. 3A and FIG. 3B.

DETAILED DESCRIPTION OF THE INVENTION

A description of example embodiments of the invention follows.

Figure 1:
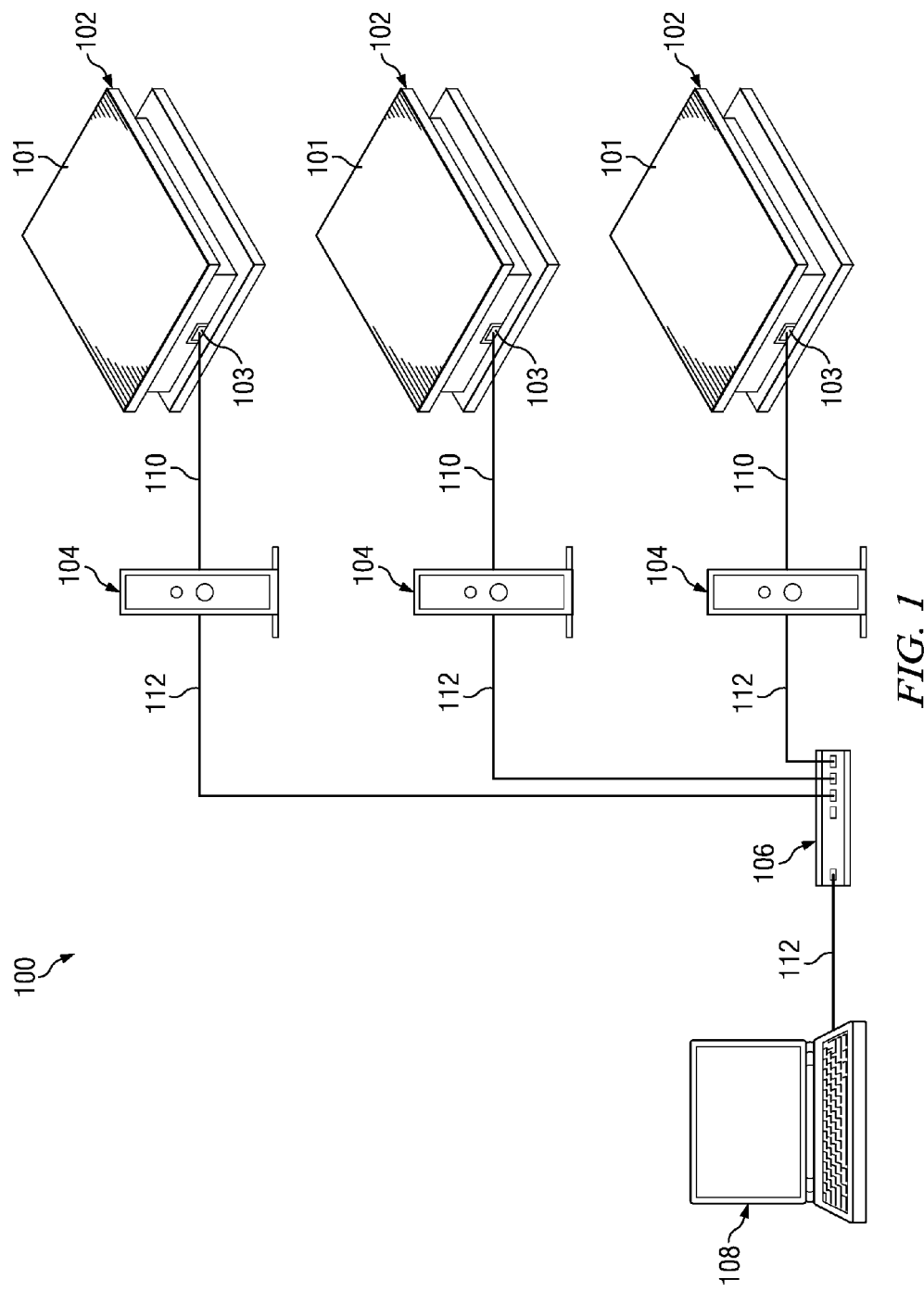
FIG. 1 is an illustration of a force platform system according to an embodiment of the invention.

FIG. 1 is an illustration of a force platform system 100 according to an embodiment of the invention. System 100 can be used to measure ground reaction forces and includes one or more force platforms 102, one or more signal conditioners 104 (which may be analog amplifiers and/or digital processors, and which can be either connected to or embedded in the force plates), and a computer 108, such as a personal computer (PC), for data collection.

Force Platform Description

Force platform 102 shown in FIG. 1 is designed to measure the forces and moments applied to its top surface 101 as a subject stands, steps, or jumps on it. Force platform 102 outputs force signals to output port 103, where platform 102 can connect to and communicate with force signal conditioner 104.

Figure 2:
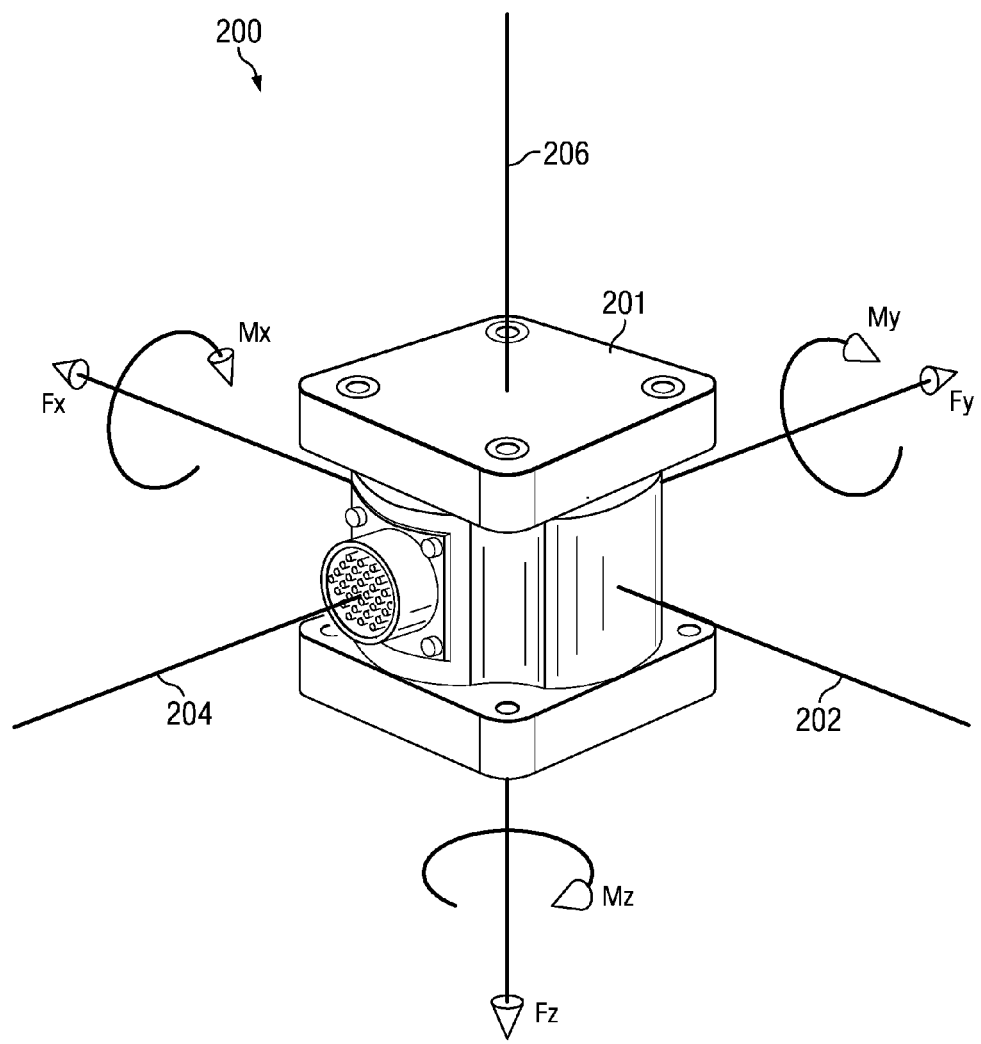
FIG. 2 is a diagram showing the three force components and the three moment components that are measured with a force platform according to an embodiment of the invention.

Force platform 102 can include one or more force transducers or load cells for measuring forces. FIG. 2 shows the three force components and the three moment components that are measured by a force transducer 200 as a subject is in contact with platform 102. For illustrative purposes, the top surface 201 of transducer 200 can be regarded as representing the top surface 101 of force platform 102 of FIG. 1. Fx, Fy, and Fz are the force components and act along the axes 202, 204, and 206 of an orthogonal x, y, z-coordinate system. In FIG. 2, the arrows point in the direction of positive force along each of the axes, following the right-hand rule. Fx and Fy are the horizontal or shear force components, and Fz is the vertical force component. Mx, My and Mz are the three torque and moment components. The torque and moments rotate around the corresponding x, y and z axes 202, 204, and 206. Positive moments are determined according to the right hand rule. When looking down an axis (in its positive direction) positive moments have a clockwise rotation.

Force platforms and load cells using strain gauges to measure applied forces are described in U.S. Pat. No. 4,493,220, by Forest J. Carignan et al., issued Jan. 15, 1985, and incorporated herein by reference in its entirety.

Signal Conditioner Description

Referring back to FIG. 1, an amplifier or signal conditioner 104 can be connected to force plate 102. For each of the three forces and the three moment components that are measured, the signal conditioner 104 supplies an excitation voltage to a set of strain gauge bridges embedded in the force platform 102. The resulting output is a low level voltage proportional to that component of the applied mechanical load. This output can be sampled by the signal conditioner 104, and various signal conditioning techniques may be applied. The signal conditioner 104 will provide digital and/or analog data streams to the connected computer 108.

Computer Description

The signal conditioner 104 can connect to a computer 108 through some sort of medium, such as an analog card, a Universal Serial Bus (USB), an Ethernet or a serial interface. As shown in FIG. 1, multiple signal conditioners 104 may be connected via USB connections 112 and USB hub 106 to a single computer 108. When the computer 108 receives the ground reaction force data, it may perform additional processing and display or save the data depending on the software program.

Features of a Force Platform System

Figure 3A:
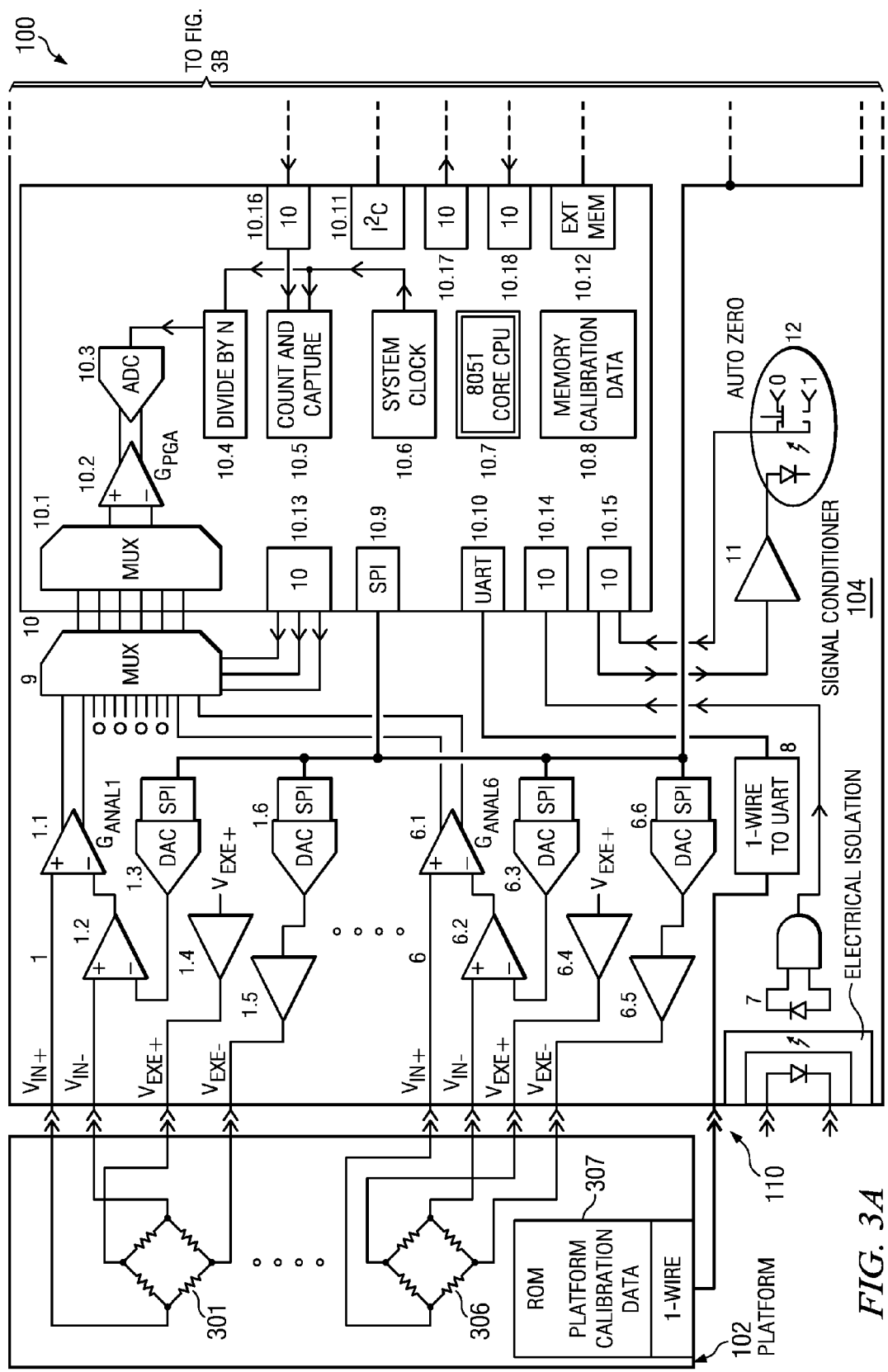

FIG. 3A and FIG. 3B together are a diagram of the hardware architecture of an embodiment of force platform system 100 including platform 102, signal conditioner 104, and computer 108. Platform 102 is connected to signal conditioner 104 via connection or cable 110, which can include connections for excitation voltages $V_{EXE+}$, $V_{EXE-}$ and output voltages $V_{IN+}$ and $V_{IN-}$ for multiple channels of force signals. As illustrated in FIGS. 3A-B, platform 102 includes six force channels associated with six strain gauges, each including a bridge circuit driven by excitation voltages and providing bridge output voltages. For simplicity, only circuitry for force channels 1 and 6, including strain gauges 301 and 306 in platform 102 and amplifiers 1 and 6 in signal conditioner 104, are shown in FIGS. 3A-B. The omitted circuitry for channels 2-5 is identical to that shown for channels 1 and 6.

Connection or cable 110 can also include a communication link, such as a 1-Wire interface, to allow signal conditioner 104 to retrieve data stored in nonvolatile memory 307 of platform 102. Nonvolatile memory 307 may be read only memory (ROM) as shown in FIGS. 3A-B, or may be programmable, including reprogrammable, memory, such as an EPROM. Nonvolatile memory 307 can store force platform calibration data and may also store a platform serial number and platform capacity.

As shown in FIGS. 3A-B, signal conditioner 104 is connected to PC 108 via a USB connection 112. A primary function of signal conditioner 104 is to condition force data from multiple strain gauge inputs and output the results as multiple analog channels and/or a multiple channel digital data stream. The analog outputs can be high level and suitable as inputs to a multi-channel analog-to-digital converter (ADC). The digital data output can be transmitted to a host PC 108 via USB connection 112. The USB connection 112 can also be used to send and receive control and status information used by signal conditioner 104. It will be understood that additional signal conditioners 104 may be connect via USB to computer 108, such as illustrated for force platform system 100 of FIG. 1. Signal conditioner 104 can receive commands and timing signals from the host PC 108 and can send digital force signals to the PC 108 via the USB connection 112. Alternatively or in addition, signal conditioner 104 can output analog force signals, illustrated in FIGS. 3A-B as $V_{OUT}$ (1-6), at an analog output port 313, which may be further connected to an input port (not shown) of computer 108 for receiving analog signals.

FIGS. 3A-B illustrate further details of the hardware components of signal conditioner 104. Signal conditioner 104 includes a microprocessor 10 for digitizing and conditioning the force signals received from platform 102 and a microprocessor 18 for communicating with PC 108 via a USB connection 112. Microprocessor 10 is connected to and communicates with microprocessor 18 via communication lines that include an I2C bus interface 10.11, an 8-bit extended memory interface 10.12, a 1-bit SOF to Count-and-Capture line 10.16, a 1-bit microprocessor to USB interface bus 10.17, and a 3-bit unidirectional asynchronous bus 10.18. Microprocessor 10 is connected to and communicates with other components of signal conditioner 104 via a Serial Peripheral Interface (SPI) bus. The SPI bus connects to microprocessor 10 at SPI Bus interface 10.9.

The signal conditioner 104 includes, for force channel 1, an analog signal conditioning circuitry 1 that is connected to the bridge circuitry of strain gauge 301 and includes a differential amplifier 1.1. One input to differential amplifier 1.1 is the bridge output voltage $V_{IN+}$ and another input is a bridge balancing voltage that is provided by the signal conditioning circuitry 1. Differential amplifier 1.1 has a gain $G_{ANAL1}$ and an output that is connected to a multiplexer 9. A differential amplifier 1.2 is connected between strain gauge 301 and differential amplifier 1.1 for inserting the bridge balancing voltage into force channel 1. A digital-to-analog converter (DAC) 1.3 is used to produce the bridge balancing voltage under the control of microprocessor 10. One input of differential amplifier 1.2 is connected to the output of DAC 1.3; the other input of amplifier 1.2 is connected to strain gauge 301 to receive the bridge output voltage $V_{IN-}$ from strain gauge 301. The signal conditioning circuitry 1 also includes a power amplifier 1.4 connected to strain gauge 301 for supplying the positive bridge excitation voltage $V_{EXE+}$ to strain gauge 301. Also included is a power amplifier 1.5 connected to strain gauge 301 for providing a negative bridge excitation voltage $V_{EXE-}$ to strain gauge 301. A DAC 1.6 connected to the input of power amplifier 1.5 is used to produce the negative bridge excitation voltage $V_{EXE-}$ under the control of microprocessor 10. Both DAC 1.3 and DAC 1.6 are connected to the SPI Bus interface 10.9 of microprocessor 10.

As shown in FIGS. 3A-B, the analog signal conditioning circuitry 6 for force channel 6 includes identical components to signal conditioning circuitry 1 for force channel 1. Conditioning circuitry 6 is connected to strain gauge 306 and includes a differential amplifier 6.1, a differential amplifier 6.2, a DAC 6.3, a power amplifier 6.4, a power amplifier 6.5, and a DAC 6.6. As with amplifier 1.1, differential amplifier 6.1 has a gain $G_{ANAL6}$ and an output connected to multiplexer 9. Similarly, both DAC 6.3 and DAC 6.6 are connected to microprocessor 10 via an SPI bus connection. Like circuitry is provided for each channel but not shown.

Multiplexor 9 is a 6-to-3 differential line multiplexor that receives the six force channels from the signal conditioning circuitries 1 through 6 and multiplexes the six channels into three differential output lines that are connected to microprocessor 10. Multiplexor 9 can receive inputs, e.g., control signals, from microprocessor 10 via a 3-bit bus connection.

In the example shown in FIGS. 3A-B, microprocessor 10 is a SILICON LABORATORIES (Silab) 8051 based mixed-signal microcontroller that comprises multiple components, including a system clock 10.6, e.g., with a nominal clock rate of 100 MHz, a 8051 based core CPU 10.7, system nonvolatile memory 10.8, e.g., for storing calibration and configuration data, and various interfaces and inputs/outputs to communicate with external circuitry. The components of microprocessor 10 are interconnected to allow for communication among the components and with CPU 10.7. For simplicity, only some of the interconnections are shown in FIGS. 3A-B.

Microprocessor 10 receives inputs, i.e., force signal inputs, from external multiplexor 9 via a 3-line-to-1-line differential multiplexor 10.1. In turn, microprocessor 10 communicates with external multiplexor 9 via a 3-bit bus interface 10.13. A programmable Gain Amplifier 10.2 having gain $G_{PGA}$ connects the output of multiplexor 10.1 to the input of a 12-bit differential input analog-to-digital converter (ADC) 10.3. Signal conditioner 104 amplifies the multiplexed analog force signal received from the signal conditioning circuitries 1 through 6 using amplifier 10.2 and converts the amplified signal to digital signals using ADC 10.3. The digitized force signals are then available for further processing, such as conditioning the signals based on calibration data. Calibration data can include calibration data retrieved from the nonvolatile memory 307 of force platform 102 and can also include signal conditioning calibration data stored in nonvolatile memory 10.8 of microprocessor 10. As shown in FIGS. 3A-B, connection 110 includes a 1-Wire communication connection between memory 307 and signal conditioner 104 for retrieving platform calibration data, platform capacity, and/or a platform serial number. Microprocessor 10 communicates with memory 307 through a 1-Wire to UART bus interface 8 which is connected to a Universal Asynchronous Receiver Transmitter (UART) bus interface 10.10 of microprocessor 10.

As described in more detail below, the ADC 10.3 is connected to a timing and synchronization circuitry that includes a programmable divide-by-N counter 10.4, a Count-and-Capture Counter 10.5, and system clock 10.6. The Count-and-Capture Counter 10.5 receives a timing signal from microprocessor 18 via 1-bit SOF to Count-and-Capture line 10.16.

As shown in FIGS. 3A-B, signal conditioner 104 can include an opto-isolator 7 for receiving a 1-bit Genlock signal from an externally connected device while providing electrical isolation from the external device. Microprocessor 10 communicates with opto-isolator 7 via a 1-bit opto-isolator to microprocessor bus 10.14. The genlock/trigger input is a multi-purpose digital input channel. In one embodiment, the connector for this input channel is an RCA phono type receptacle. For example, the input range can be 0 to 10 V with the low state being less than 1 V and the high state being greater than 3 V. In addition, the hardware of signal conditioner 104 may support two software configurable operating modes: genlock or generic digital input.

Genlock is a common technique where the output of one source is used to synchronize multiple devices. For example, in genlock mode signal conditioner 104 may transmit a single dataset on either the rising or falling edge of the genlock signal to a connected device, e.g., PC 108 connected via connection 112. When the genlock/trigger input is operating as a generic digital input, the state of the input can be captured and transmitted in the digital output data stream of signal conditioner 104.

Signal conditioner 104 can include an auto zero button 12 that includes a switch and an LED driven by an amplifier 11. A 2-bit bus 10.15 connects microprocessor 10 to auto zero button 12 and amplifier 11. The auto-zero button 12 can be a multi-purpose button. For example, button 12 can be used to zero signal conditioner 104 or place signal conditioner 104 into diagnostic mode. The signal conditioner 104 may be zeroed by pushing the auto zero button 12 and immediately releasing it. In addition, the signal conditioner 104 may be zeroed through software. Using either method, the LED driven by amplifier 11 will flash once to confirm the zero action. To place the amplifier into diagnostic mode, a user may press and hold the auto-zero button 12 down until the LED starts to blink, then release the button. The LED, for example, will continue to blink until diagnostic mode is terminated.

As shown in FIGS. 3A-B, signal conditioner 104 includes analog reconstruction circuitry for outputting six channels of conditioned or processed analog force data at analog output port 313. For simplicity, only analog reconstruction circuitries 13 and 17 for analog force channels 1 and 6, respectively, are shown. The circuitries for analog channels 2-5 are identical to those for channels 1 and 6. For processed analog channel 1, signal conditioner 104 includes analog reconstruction circuitry 13 for outputting processed analog data corresponding to force platform channel 1, i.e., force signals detected by strain gauge 301. Analog reconstruction circuitry 13 includes digital-to-analog converter (DAC) 13.1 connected to analog reconstruction amplifier and filter 13.2, whose output is processed analog force signal $V_{OUT1}$ at port 313. For processed analog force channel 6, signal conditioner 104 includes analog reconstruction circuitry 17 that includes elements identical to elements 13.1 and 13.2 of circuitry 13. Analog reconstruction circuitry 17 includes DAC 17.1 connected to analog reconstruction amplifier and filter 17.2. Circuitry 17 outputs the processed analog force signal $V_{OUT6}$ at port 313. All digital-to-analog converters in the reconstruction circuitry, e.g., DAC 13.1 and DAC 17.1, are connected to microprocessor 10 via the SPI bus.

In the example shown in FIGS. 3A-B, microprocessor 18 is a CYPRESS 8051 based USB interface microprocessor. Microprocessor 18 is electrically isolated from other components of signal conditioner 104, such as microprocessor 10. Microprocessor 18 comprises various processing and communication elements, including a 8051 based core CPU 18.1 and a USB interface 18.10 to communicate with PC 108 via USB connection 112. The USB interface 18.10 provides a USB Start of Frame (SOF) signal 18.3 that is passed to programmable divide-by-N counter 18.2. A 1-bit bus 18.8 connects an output of the divide-by-N counter 18.2 of microprocessor 18 to an input of count-and-capture counter 10.4 of microprocessor 10.

Also included in microprocessor 18 are a USB control endpoint 18.4 and a USB bulk endpoint 18.5, both of which are connected to USB interface 18.10. A FIFO interface is connected to USB bulk endpoint 18.5 for communication between microprocessors 10 and 18. The FIFO interface 18.6 is connected to interfaces 10.12 and 10.18 of microprocessor 10. In addition, microprocessor 18 includes I2C interface 18.7 for connecting USB control endpoint 18.4 to microprocessor 10. Interface 18.7 is connected to I2C interface 10.11 of microprocessor 10. Additional communication between microprocessors 10 and 18 is provided via a 1-bit bus 18.9 that connects FIFO Full to interface 10.17 of microprocessor 10.

The force platform system 100 is an efficient way to define the geometrical organization of the platforms 102 and the organization of the data. Force platform system 100 facilitates organizing and coordinating the individual components of a single or multi-platform system allowing for easy setup, configuration, and reconfiguration as the testing environment changes. Features of the force platform system 100 are discussed below.

1) Correct calibration parameters are applied transparent to the user.

Traditionally, when the configuration of a force platform system is changed, additional setup is required in software to complete the process. This involves loading the calibration information for each system component and testing to verify the amplifier, amplifier calibration tables, platform, and platform calibration tables are correctly synchronized together. Force platform system 100 both simplifies setup and reduces configuration error because of the following features:

a) Each component of the force platform system 100, platform 102 or conditioner 104 can have its complete calibration information stored on the device itself.
b) The force platform system 100 can be configured such that when the individual components are connected together the correct calibration information becomes automatically available where needed.

The above features can eliminate the possibility of having calibration information matched to the wrong component. Each component, when connected to any other component, assures that the correct calibration information is transferred without user intervention. Setup time is also reduced as no manual installation of calibration information is required.

2) Data from all platforms can be synchronized in time.

In a multiple force plate system, such as shown in FIG. 1, it is preferable that data sampling is synchronized across all platforms 102. Otherwise, it may be difficult to establish a reasonable timeline for examining the applied ground reaction forces. In a typical analog acquisition system the problem can be solved by the analog to digital converter (ADC) card which resides in the PC. Each amplifier sends an analog signal to the ADC card; a crystal controlled clock in the ADC card times the periodic sampling of data across all channels.

For digital acquisition systems the solution is more complex. The data sampling rate is still controlled by a crystal controlled clock, except the clock now resides on the individual signal conditioner. A six signal conditioner system, for example, may use six clocks. The problem is that all clocks contain a small amount of accuracy error. This error may be small, but it is cumulative over time. The effect is called skew; eventually some signal conditioners will have taken more data samples than others.

The force platform system 100 uses a novel method to synchronize the crystal control clocks in each signal conditioner 104 to the master universal serial bus (USB) clock in the PC 108. This technique not only achieves data synchronization across multiple platforms 102 but does so with no additional setup, wiring or user intervention. This technique is described in more detail below with reference to FIGS. 8 and 9.

3) The relationship between the platform physical layout configuration and the data storage format may be easily definable and implemented transparent to the user.

Many gait laboratories use multiple force plates or platforms to capture the reaction forces and moments generated throughout a full gait cycle. Two and four-platform setups are the most common installations. The layout of a gait lab's force plates is largely dependent on the stride length of its subjects, as children clearly require closer platform spacing than adults. FIGS. 4A-E illustrate some common force platform configurations. Both the physical layout and the order in which the force platforms are traversed by the test subjects may vary. The gray platforms in FIGS. 4A-E indicate the number and position of the minimum platforms for each layout; white platforms show the location of additional recommended platforms. Three- or four-platform installations are generally preferred as they increase the number of foot strikes captured during the patient's gait cycle. FIGS. 4A-E show foot strikes 402, 404 on force plates 102, with 402 being a foot strike with the left foot and 404 a foot strike with the right foot.

Figure 4A:
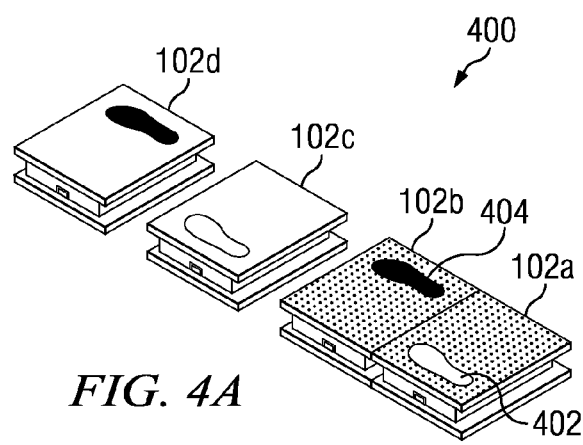
FIGS. 4A-E illustrate different force plate configurations that can be used for multiple platform gait studies.
Figure 4B:
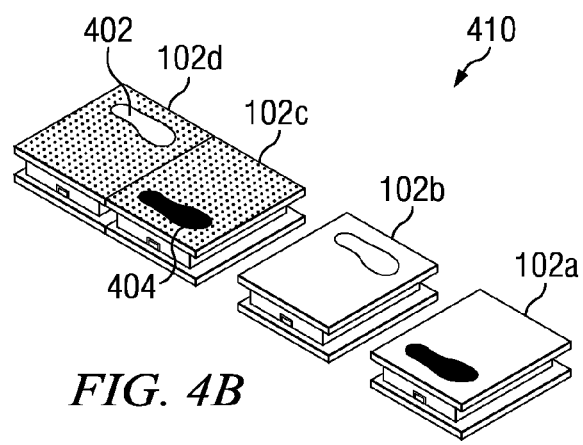

FIG. 4A illustrates an inline configuration 400 that is used in a large number of gait labs as it provides a "corridor" where patients are less tempted to aim their foot strikes, thus changing their gait patterns. Configuration 400 includes four platforms 102*a*, 102*b*, 102*c*, 102*d* placed in a straight line. Platform spacing can be adjusted for step length variability, patients' age or application (walking, running, sports, etc.). For example, it may be preferred that only one foot strike, 402 or 404, occur per platform, such as illustrated in FIG. 4A. If subjects turn around and walk in the opposite direction, the order in which the force plates 102*a-d* are traversed is reversed as illustrated in configuration 410 shown in FIG. 4B. When changing from configuration 400 to 410, the force platform system 100 allows for the automatic re-ordering of platforms 102*a-d* by simply having a subject traverse the platforms in the desired sequence. Although not shown, each of the platform configurations 420, 430 and 440 of FIGS. 4C, 4D and 4E may be traversed in reverse order. Additional details of the platform ordering feature are as described below.

Figure 4C:
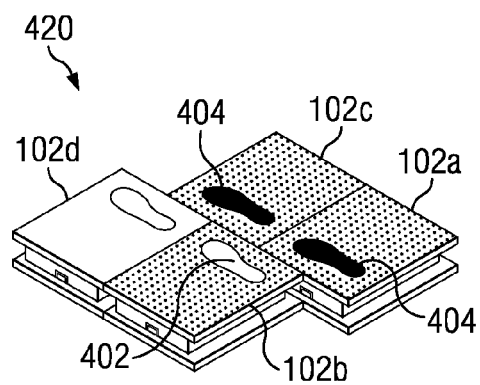

FIG. 4C illustrates a staggered configuration 420 that is common in the gait community, although it may be employed less often than the inline arrangement. Configuration 420 includes four platforms 102*a*, 102*b*, 102*c*, 102*d* arranged in staggered pairs. Configuration 420 allows for adaptation to different step widths, which is often required when working with elderly patients due to their need for a larger base of support.

Figure 4D:
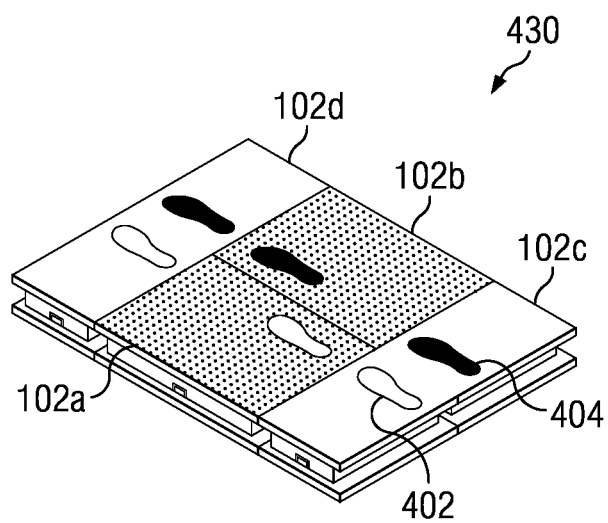

FIG. 4D illustrates a configuration 430 that can be used to record patients' center of pressure (COP) patterns while initiating or terminating gait, as well as reaction times and movements during postural perturbations or secondary tasks. Gait initiation, gait termination, and fall prevention have become intensively studied protocols intended to test the effect of a central or peripheral disease on the sensorimotor functions. Configuration 430 includes two parallel platforms 102*a*, 102*b*, which are flanked on both ends by two additional platforms 102*c*, 102*d*. Platforms 102*c* and 102*d* are rotated 90 degrees with respect to platforms 102*a* and 102*b*. In an embodiment, force platform system 100 allows for rotational transformation of the force signals in a signal conditioner 104 connected to a platform 102, simplifying the collection of force data from multiple platforms that have different orientations.

Figure 4E:
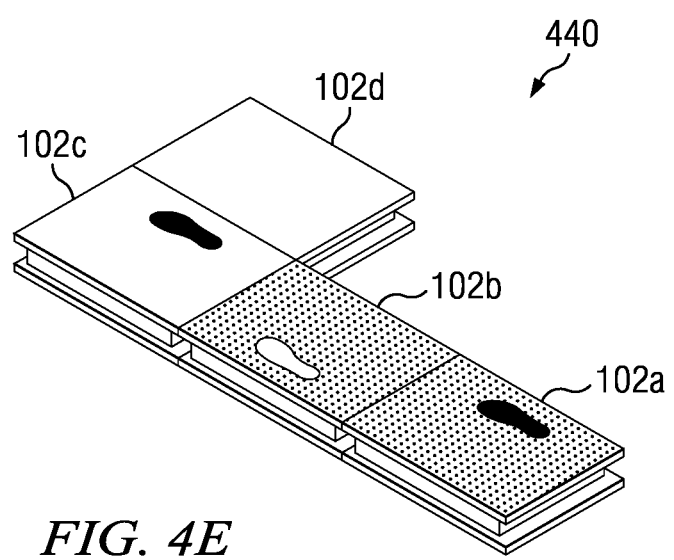

FIG. 4E illustrates an inline configuration 440 using large force plates 102*a*, 102*b*, 102*c*. Configuration 440 can be used for sport activities that involve multiple foot strikes over a long distance, such as running and jumping. The addition of an adjacent platform 102*d* allows for the study of side-step cutting and activities that involve a large base of support.

For gait analysis a defined relationship between platform layout and data storage format is necessary. If this relationship is not defined it is difficult to verify that the test subject performed according to protocol, and additional analysis may be required to determine the order of footfall. Traditionally re-defining the relationship between platform layout, and data storage format could involve reconfiguring both hardware and software. The force platform system 100 resolves these issues by providing the following:

a) A designated platform order is definable and this order dictates the data storage format (e.g. the order in which data from the platform is presented).

b) The designated platform order may be set by having a subject traverse the platforms in the desired sequence.

The force platform system 100 achieves these two goals by inserting a software layer between the proprietary or third party acquisition software and the signal conditioners. This software layer receives the data and formats it in a predefined format. It is then made available through a common interface to the proprietary or third party vendor. The predefined format is determined by running a software program that employs threshold detection to determine the order of platform loading. This order is then stored and applied to future trials. The software layer and its communication with other system components is further described with reference to FIG. 11 below.

The Mathematics of the Force Platform System

Referring back to FIG. 2, the force components that act along the axes of the force plates orthogonal x, y, z coordinate system are designated Fx, Fy, and Fz. The moment and torque components which rotate around each force axis are designated Mx, My and Mz. Force platform 102 provides six channels of output. Each channel represents one of the six components of applied load, the three orthogonal forces and the three orthogonal moments and torques. Crosstalk occurs when some portion of applied load to one channel appears in the output of another. This residual output is caused by the mechanical/electrical limitations of the measuring device and can be corrected for. This is done by applying known force, moments and torques to each platform 102 at key positions and recording the output across all channels. From this output a 6 by 6 calibration matrix is derived (see Table 1 below). This matrix is then used to both convert the output from each channel into engineering units and to correct for crosstalk.

Platform 102 in the force platform system 104 stores a platform identification and calibration matrix in non volatile memory (see FIGS. 3A-B). When a force platform 102 is connected to a signal conditioner 104 the calibration matrix becomes available to the signal conditioner 104, which stores its own calibration settings in non volatile memory (see FIGS. 3A-B, memory 10.8).

When recording data, the signal conditioner 104 reads mV inputs from each platform output channel, and converts them to engineering units. When doing this the signal conditioner 104 uses calibrated gains and excitations, and provides crosstalk corrections by applying the calibration matrix. The signal conditioner 104 digital output stream to the PC 108 consists of fully processed IEEE floating point numbers presented in their respective engineering units.

The signal conditioner 104 performs extensive numerical processing which includes: using factory calibrated constants in place of nominal values for gains and excitations, correcting for cable losses due to finite bridge resistances, and providing crosstalk corrections by applying a factory calibrated platform correction matrix. Signal conditioner 104 can remove a DC offset, implement a user defined DC set point, and perform rotational transformation to compensate for physical platform placement considerations.

The following formula is used internally by the signal conditioner 104 to convert the platform channel outputs into engineering units.

$$F_{chan} = \frac{(I_{ADC} \times V_{Ref} \times 10^6 \times C_{chan,col})}{(V_{exc} \times \text{gain} \times I_{FS})}$$

where the terms $F_{Chan}$, $I_{ADC}$, $C_{chan,col}$, $V_{exc}$, and gain are channel specific and:

ADC: Analog to digital converter $F_{Chan}$: The force or moment output in engineering units for a given channel $V_{Re\,f}$: The reference voltage of the signal conditioner ADC $I_{FS}$: The full scale integer output of the signal conditioner ADC $I_{ADC}$: Integer output of the ADC for a particular data sample col: A column index to the calibration matrix $C_{chan,col}$: The sensitivity value from the calibration matrix. The chan subscript refers to the row. The col subscript refers to the column.

$V_{exc}$: The excitation voltage gain: The gain value

An exemplary calibration matrix is shown in Table 1. A calibration matrix, also referred to as a sensitivity matrix, is supplied with platform 102. The calibration data can be stored in nonvolatile memory and may be programmable and retrievable by external electronics, e.g., signal conditioner 104. To use the sensitivity matrix to calculate $F_{chan}$ for each of the three orthogonal forces and the three orthogonal moments and torques, one can sum over all columns using the appropriate $C_{chan,col}$ terms for each channel.

TABLE 1

Sample Calibration Matrix

| | Sample Calibration Matrix Channel | | | | | |
|---|---|---|---|---|---|---|
| | 0 VFx | 1 VFy | 2 VFz | 3 VMx | 4 VMy | 5 VMz |
| | Input to channel i(lb, in-lb) is B(l, j)times the electrical output j(uV, Vex) BP 400600-2000 | | | | | |
| Fx | 0.6519 | −0.0068 | −0.0019 | 0.0009 | −0.0017 | −0.0003 |
| Fy | 0.0090 | 0.6515 | −0.0037 | 0.0009 | 0.0005 | 0.0010 |
| Fz | 0.0018 | 0.0017 | 2.5523 | −0.0062 | 0.0001 | 0.0026 |
| Mx | −0.0044 | −0.0032 | 0.0003 | 12.8281 | 0.0108 | −0.0138 |
| My | 0.0725 | −0.0032 | 0.0003 | 0.0058 | 10.1358 | −0.0140 |
| Mz | 0.0649 | 0.0821 | 0.0792 | 0.0123 | 0.0340 | 5.4451 |

Firmware Outline

Figure 5:
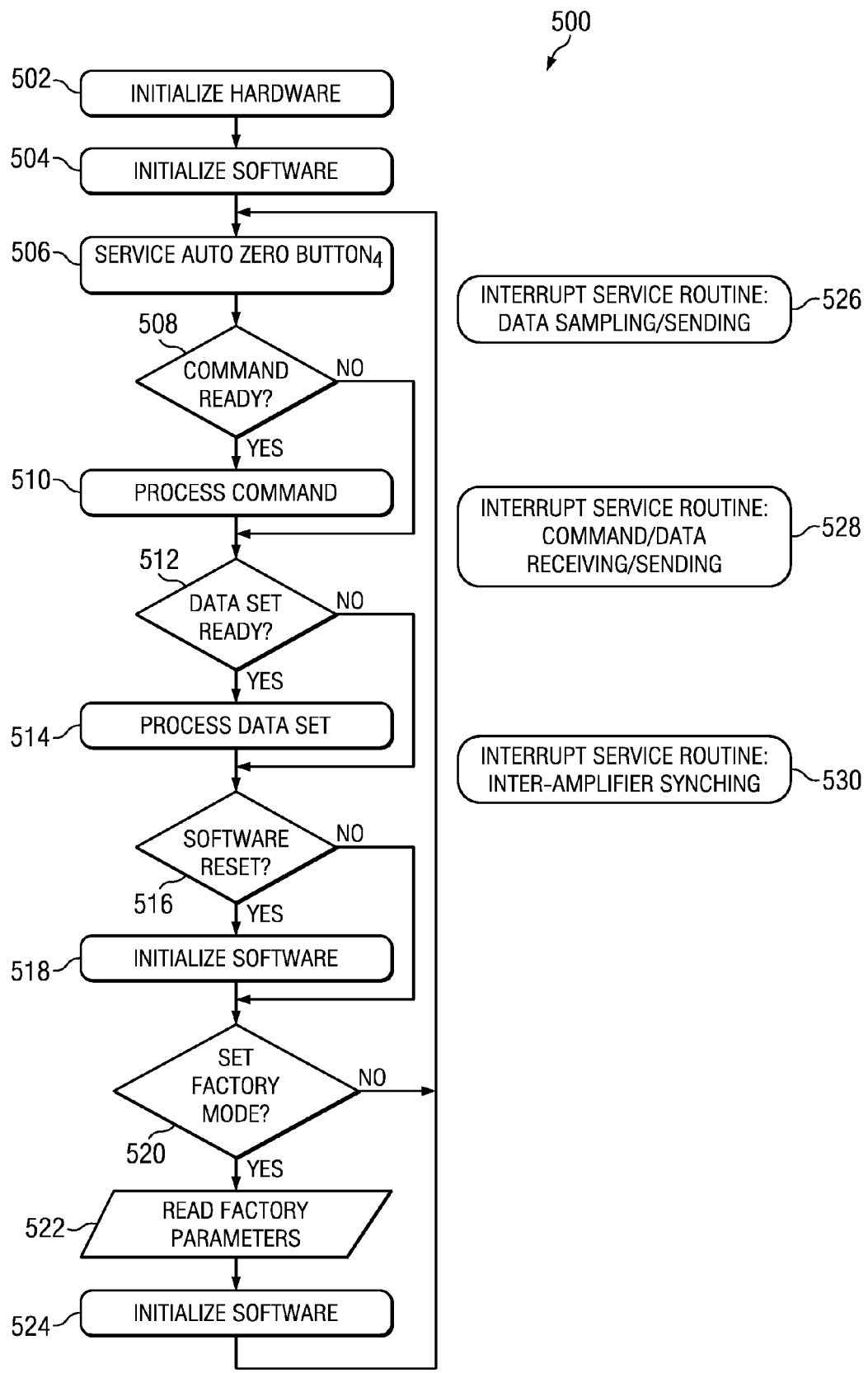
FIG. 5 is a flow diagram of the signal conditioner firmware.

FIG. 5 shows a flow chart 500 of the firmware executed by the signal conditioner 104. The primary function of the firmware is to acquire a data set consisting of six channels of raw force and moment data from a force plate 102, process the data set into useable force and moment data and output the results to a host computer 108 via the USB or analog channels. This function is performed repeatedly in a firmware loop which is timed by data set acquisition via routine 526. The supporting functions are initialization, via routines 502, 504, 518, and 524, responding to press of an auto-zero button on the signal conditioner 104, via routine 506, receiving and executing commands from the host computer (PC), via routines 528 and 510, and implementing an inter-signal conditioner synchronization scheme, via routine 530. There is also a diagnostic mode which is entered by the signal conditioner 104 in response to an extended press and hold of the auto-zero button. These processes are described in more detail below.

Hardware initialization 502 comprises the following steps:

Configuring the master system clock 10.6 to run at 100 MHz. This clock is used for all timing functions including CPU 10.7 execution speed.

Configuring all CPU I/O ports.

Reading and checking the signal conditioner 104 non-volatile memory 10.8. This memory saves the last saved signal conditioner 104 configuration.

Configuring the internal ADC 10.3. This includes setting up a sample timing clock, which runs independent of CPU control and configuring the ADC 10.3 to generate an interrupt on sample acquisition. The sample timing clock can include Count and Capture block 10.5 and Divide by N block 10.4 of microprocessor 10, and can include Divide by N counter 18.2 of microprocessor 18.

Configuring the host PC 108 command reception to generate an interrupt.

Configuring signals from the host PC 108 used for inter-amplifier synchronization to generate an interrupt.

Reading the data from a force platform 102 connected to the signal conditioner 104. This includes platform identification data and coefficients necessary for converting raw platform data to useable force and moment data.

FIGS. 3A-B illustrate a schematic of the signal conditioner 104 hardware showing hardware blocks, including microprocessors 10 and 18 and their respective subcomponents, involved in the above steps.

Software initialization 504 includes pre-calculation of all coefficients necessary for converting a raw platform data set into a useable force and moment data set. Parameters used in this calculation include signal conditioner hardware calibration values, user specified acquisition settings and platform coefficients. A last step in initialization is to set the hardware to reflect all user specified settings, enable sampling and interrupts. If the signal conditioner 104 is connected to a host 108 via the USB, it signals to the host USB that it is present (and performs a USB enumeration when queried by the host USB interface) at this time.

After hardware and software initialization routines 502 and 504, the CPU enters a firmware loop. Loop processing is interrupted by data acquisition, host command reception and host synchronization signals. Synchronization signals trigger actions in the data acquisition interrupt service routine 530 (described in another section below). Acquisition of an entire data set by interrupt service routine for data sampling/sending 526 or a host command reception by the interrupt service routine for command/data receiving/sending 528 set flags which trigger an appropriate action in the loop.

The Service Auto Zero Button routine 506 handles signals from the auto zero button. When the user momentarily presses the auto zero button 12 (see FIGS. 3A-B), the signal conditioner 104 determines the optimal operating point for its hardware bridge balancing circuitry and also performs a tare of any remaining DC signals in the platform data channels. These current tare values are subtracted from platform raw data prior to any further digital processing. If the user presses and holds the auto zero button down for over three seconds, the signal conditioner 104 enters a diagnostic mode where all configuration data is set to a factory preconfigured state.

Upon completion of an entire force platform data acquisition set, the CPU takes the data and converts it to a force platform force and moment data set. The calculations performed are outlined above. In the firmware loop, branch point 512 looks for a flag that indicates a complete data set is acquired and ready. If a data set is ready, the loop enters the Process Data Set routine 514 to convert the data to a force and moment data set as described above.

A software reset is performed whenever a recalculation of the pre-calculated coefficients used for data set processing is required. This can occur whenever the user resets a signal conditioner setting or a factory reset. In the firmware loop shown in FIG. 5, this is shown by the branch points Software Reset 516 and Set Factory Mode 520. Software Reset branch point 516 directs processing to Initialize Software routine 518, which can perform the calculations described above with reference to the Initialize Software routine 504. The Set Factory Mode branch point 520 directs processing to Read Factory Parameters routine 522 and Initialize Software routine 524 to reset the signal conditioner 104 to factory settings.

Synchronization of Data Acquisition among Multiple Signal Conditioners

The signal conditioner 104 is a digital data acquisition device employing the Universal Serial Bus (USB) for connection to a host computer (PC). The signal conditioner 104 amplifies and filters time varying voltage data from six strain gauge channels, periodically samples the data, digitally processes the sampled data and sends the resultant data to a host PC via USB. In one embodiment, signal conditioner 104 utilizes a novel scheme for synchronizing digital data acquisition across multiple USB data acquisition devices (USBDACs) via existing signals on the USB. Methods and systems for synchronizing actions of devices connected to a host, such as a USB host, are described below. First, the conditions which cause a synchronization to occur are discussed. The synchronization scheme and its implementation in the signal conditioner 104 hardware are then presented. Finally, the advantages of this scheme are listed.

The fundamental purpose of digital data acquisition is to sample an analog signal. Typically the sampling is done periodically in time across multiple channels of analog data. In this case it is important that each channel be sampled at the same time (or that there is a known constant delay between sampling of successive channels). The hardware device that converts analog data to a digital number is called an Analog-to-Digital Converter (ADC). A USBDAC contains an ADC, a sample timing clock and a USB interface for connection to a host PC with appropriate data acquisition software. When data from multiple channels are sampled by a single USBDAC, synchronization (i.e. simultaneous sampling of each channel or a known, constant delay between channels) is ensured because a single sample timing clock is used.

Now consider a system comprising a host PC and multiple USBDACs, with each USBDAC having its own ADC, sample timing clock and USB connection for communicating with the host PC. The USBDACs are all instructed to sample at the same rate by the host PC; sampling is then initiated by the PC and each USBDAC begins to periodically sample and send data sets to the PC. Preferably, the data from all USBDACs are synchronized in time. The force platform system 100 may be implemented in such a system, where the USBDACs are signal conditioners 104 connected to PC 108. Two issues arise in such a system.

The first is the question of whether or not a single sample initiation command can be issued to all USBDACs simultaneously and if not, whether or not the order and delay between serially issued start commands is known. For USBDACs neither is true.

The second issue is the effect of small disparities in sample clock rates among the multiple USBDACs. The following example demonstrates this effect. Consider two USBDACs and their respective sample clocks: USBDAC#1 with sample clock running at rate $R_1=1000.000$ Hz and USBDAC#2 with $R_2=1000.050$ Hz. The 1000th sample for the USBDAC #1 will occur at $(1000/R_1)=1.0$ s, while the 1000th sample for USBDAC #2 will occur at $(1000/R_2)=0.99995$ s, or 50 µs earlier. This delay or skew between sample times grows linearly with time.

Note that in addition to introducing a set of unknown and unequal delays in the arrival times of start commands issued to multiple USB devices, the inability to simultaneously broadcast a single command to multiple USB devices also eliminates the possibility of periodically synchronizing or "lining up" the devices.

The USB employs well defined hardware and software protocols that are implemented by manufacturers of PC and USB device hardware and software. The internal details of these protocols are typically transparent to the user of these devices. One such detail is the USB Start of Frame (SOF) signal and counter. The SOF signal can be used to circumvent the two problems described above. For the following discussion the following information about the SOF signal is pertinent. The SOF signal is generated by the host PC USB hardware and is sent to all devices at a constant defined interval, the SOF interval. The SOF signal is received by all connected USB devices at the same time. Its main function is to establish time frames for USB traffic to and from the host PC to connected USB devices. For full speed USB devices, the SOF signal is sent every 1.0 millisecond; for high speed devices the SOF is sent every 125 microseconds (µs). Associated with the SOF signal is a Frame Number. The Frame Number is generated by the host PC and is used to identify the current frame. The Frame Number is contained in 11 bits and rolls over to 0 when it reaches $(2^{11}-1)$. The current Frame Number is embedded in each USB frame and is sent to each connected USB device every frame.

The SOF signal can be used to simultaneously start multiple USB devices using the following scheme. When preparing to serially issue start commands issued one each to multiple devices, the host device first inspects the current Frame Number. It then calculates the Frame Number for a SOF signal which will occur sufficiently far enough in the future to allow enough time for all the serially issued start commands to reach their respective devices. The host embeds this Frame Number in each start command. The start command is then interpreted by the devices to mean "start on the SOF signal with this Frame Number" (as opposed to "start when this command is received"). To avoid ambiguity due to roll over of the current Frame Number, all serially issued start commands must reach their targets in less than $2^{11}$ frame intervals or else the number of Frame Number rollovers to wait after "the SOF signal with this Frame Number" must be also be embedded in the start command.

The SOF signal can be also be used to correct for differences in sample rates among multiple USBDACs. Before discussing this scheme the following background concerning sample timing clocks is presented. As described above, sample timing clocks are used to time periodic sampling. Sample timing clocks are often implemented in hardware as "Divide by N" counters.

Figure 6:
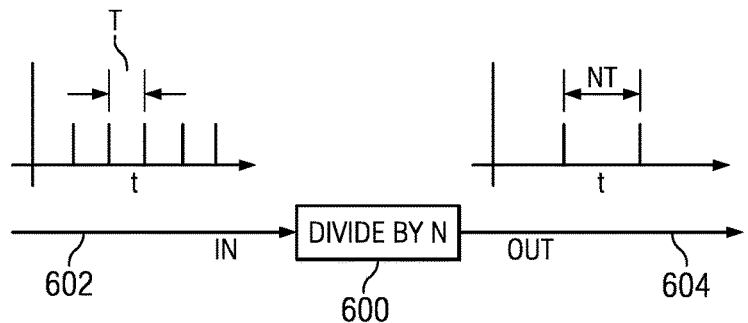
FIG. 6 is a functional diagram of a "divide by N" counter.

FIG. 6 is a functional diagram of a "Divide By N" counter. The divide by N counter 600 has an input clock signal 602 and an output clock signal 604. The output clock rate is equal to the input clock rate divided by N. In the diagram shown in FIG. 6 the input clock is 1/T, the output rate is 1/(N×T)).

The division process is implemented using two registers (a register is a device in which data of a finite value can be stored and manipulated). One register is the counting register; each time an input clock signal is detected, the number in the counting register is decremented by 1. The other register is the reload register. Each time the counting register reaches 0, an output clock signal is generated and the value in the counting register is set to the value in the reload register. Divide by N counter 600 can thus generate multiple output rates 604 from a single rate input clock 602.

Figure 7:
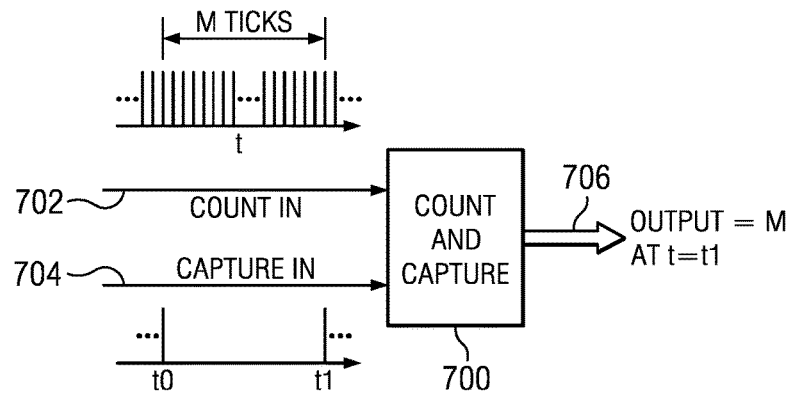
FIG. 7 is a functional diagram of a "Count and Capture" counter.

It is also convenient at this time to introduce a "Capture and Hold" or "Count and Capture" counter. FIG. 7 is a functional diagram of a "Count and Capture" counter 700. This type of counter uses one register to count low to high signal transitions ("clock ticks") at one input 702. At a low to high signal transition at a second input 704, the value in the counting register is transferred to a capture register and the counter is reset. Essentially, the count and capture counter 700 continuously counts and reports its last count value 706 when requested.

Now consider a USBDAC equipped with the following hardware: an ADC, one system hardware clock running at a nominal rate $F_{SYS}$, a Divide by N counter for generating a variable rate sampling clock from the system clock, a second Divide by N clock and a Capture and Hold clock. Also, the USBDAC has a USB hardware interface which makes the USB SOF signal and the Frame Number available.

Figure 8:
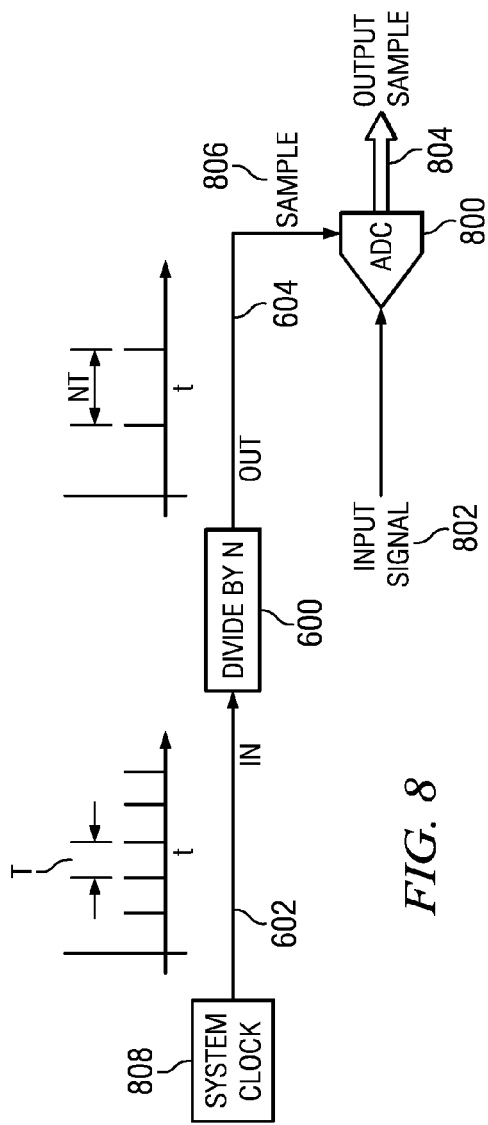
FIG. 8 is a functional diagram of an analog to digital converter (ADC) and sample timing hardware.

FIG. 8 is a functional diagram of an ADC 800 and sample timing hardware. The system hardware clock 808 and one Divide by N counter 600 are used to time ADC 800 sampling of input signal 802. The sample rate is equal to $F_{SYS}$/N. ADC 800 sampling is initiated at its SAMPLE input 806 to sample input signal 802 and output the sampled input signal at output sample 804.

Figure 9:
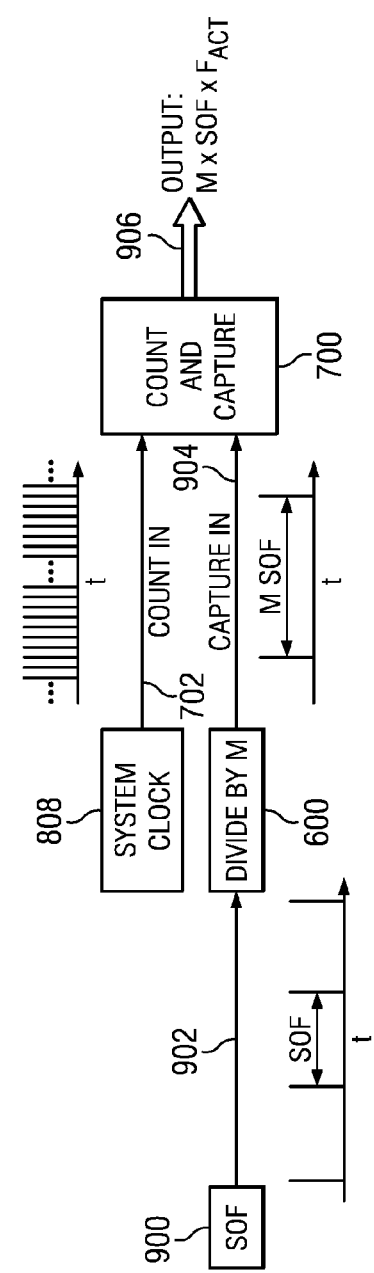
FIG. 9 is a functional diagram of synchronization hardware.

As shown in FIG. 9, the system hardware clock 808 is also connected to the counting input 702 of Capture and Hold counter 700. The Capture signal 904 is the SOF signal 900 passed through a Divide by M counter 600. Thus the Capture and Hold counter 700 is continuously counting system clock ticks during intervals equal to M SOF intervals. The SOF interval is known: 625 µs (assuming high speed USB). If the system hardware clock 808 is running at its nominal rate, $F_{SYS}$, the number of system clock ticks in this interval is M×$F_{SYS}$×625 µs. This calculated number of system clock ticks is compared with the actual counted number captured as diagramed in FIG. 9. Assume k more clock ticks were counted than calculated. This means the system clock is running faster than its nominal rate. The reload value in the sample timing Divide by N counter (see FIG. 8) is then increased by k for one sample period. This delays the next sample time by k system ticks. After this sample period, the reload value is replaced by its original value. The result is after every M×625 µs the USBDAC sample clock is synchronized ("lined up") with a clock running at the exact nominal rate of its system hardware clock. Using the same scheme in a multiple USBDAC system would thus eliminate the effects of slightly different USBDAC system clock rates.

The schemes described above are implemented in the signal conditioner 104 in firmware and hardware. The signal conditioner 104 contains two 8051 based microprocessors (see FIGS. 3A-B, units 10 and 18). Microprocessor 18 is used as a USB interface controller. Microprocessor 18 includes Divide by N counter 18.2 receiving a SOF signal 18.3 as an input clock signal and providing reduced rate output clock signal at 18.8. Microprocessor 10 is used for sampling and digital processing and includes ADC 10.3, Divide by N counter 10.4, Count and Capture counter 10.5, and system clock 10.6. The hardware required for the above scheme is integral to the two microprocessors 10 and 18.

This scheme has the following advantages:
The scheme runs essentially without processor control as the counters run independent of the microprocessor once they are set up. An Interrupt is generated only when microprocessor intervention is necessary.
When the signal conditioner 104 is not connected to the USB, no interrupts are generated so the microprocessor simply continues with the normal firmware.
Jitter in the SOF signal is reduced by counting system clock ticks over a number of SOF intervals.
Inter-Amplifier asynchronization, e.g. asynchronization between two or more signal conditioners 104, has been reduced to less than 2 µs over 24 hours.
The scheme works without any signal conditioner specific measurements.

Figures 10A, 10B:
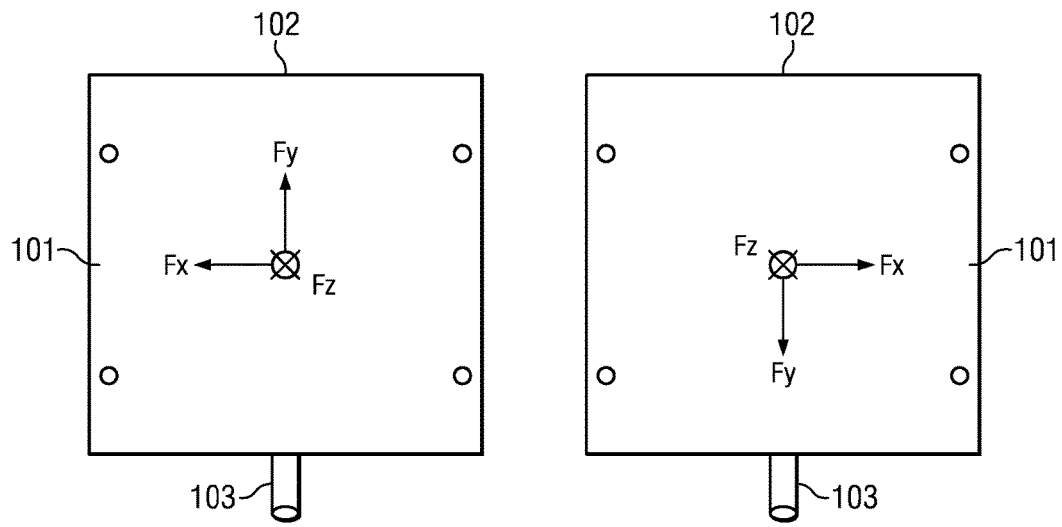
FIG. 10A illustrates the standard orientation of the x and y axes of the force platform.
FIG. 10B illustrates the rotational transformation of the x and y axes of the force platform of FIG. 10A.

FIGS. 10 A-B show top views of a force platform 102 having top surface 101 and port 103 for connecting to a signal conditioner. FIG. 10A illustrates the standard orientation of the x and y axes of force platform 102, which determines the sign and magnitude of the x and y force components Fx and Fy of an applied force. The y axis is aligned with the center of the platform and port 103, with positive y pointing away from the center in a direction directly opposite to the location of port 103. As shown in FIG. 10B, Fy is pointing up, away from port 103, and Fx is pointing to the left of and at a right angle to Fy. FIG. 10B illustrates the rotational transformation of the x and y axes, and force components Fx and Fy, of the force platform 102 of FIG. 10A. The x and y axes in FIG. 10B are rotated by 180 degrees with respect to those in FIG. 10B. In the force platform system 100, this rotational transformation can be set up and performed in a signal conditioner 104 connected to platform 102. This allows a user to physically rotate a platform and set up the signal conditioner to compensate for the rotation by simply specifying the angle of rotation for performing a rotational transform on the force signals. This saves the user from performing the transformation arithmetic on the data after the data have been collected and stored on the computer. The ability to rotationally transform force data in the signal conditioner 104 allows a user to set up an absolute coordinate system, for example, in a gait laboratory, that is independent of the physical orientation of any of the force platforms from which data are collected.

Figure 11:
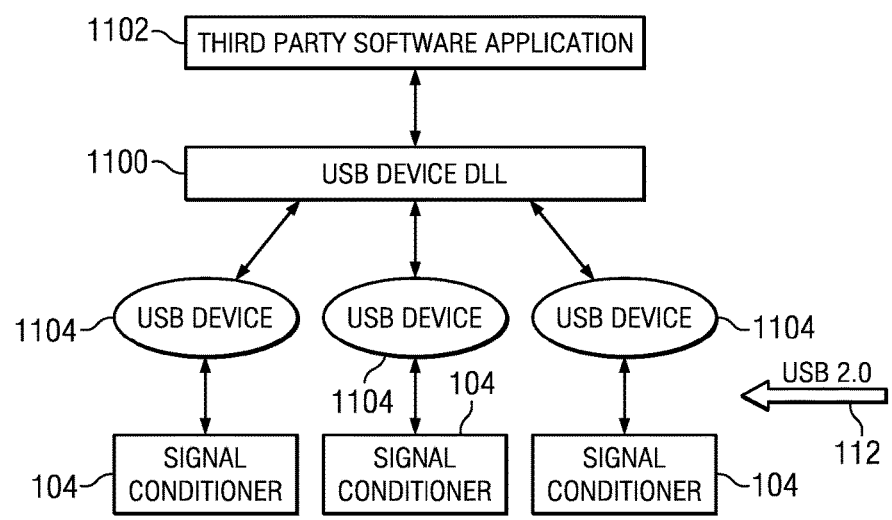
FIG. 11 is a block diagram illustrating the communication between software components and signal conditioners according to an embodiment of the invention.

FIG. 11 is a block diagram illustrating the communication between software components and signal conditioners according to an embodiment of the force platform system 100. Software layer 1100 handles all communication between a third party software application 1102 and the device drivers 1104, which in turn communicate with connected devices, such as signal conditioners 104. Software layer 1100 can be implemented as a dynamic linking library (DLL). Device drivers 1104 can be USB device drivers, such as CYPRESS USB device drivers, which communicate to signal conditioners 104 via a USB interface. The software layer 1100 can initialize and run force signal processing from platforms 102 that are connected to signal conditioners 104, which can include ordering the platforms 102 and setting a data storage format. For example, a data storage format can be set up to store data in the order in which the platforms are ordered. The software layer 1100 can perform an initialization process including the steps of receiving data distinguishing the force platforms 102, monitoring force data signals from each of the force platforms, and identifying each of the platforms to a force platform data process application, such as application 1102, by a sequence of received above-threshold force data signals. Subsequent to the initialization, software layer 1100 can process subsequent force data signals according to the identification of each of the force platforms 102. The distinguishing data can include data retrieved from nonvolatile memory of each of the force platforms 102. The retrieved data can include platform serial number, calibration data, and platform capacity.

The teachings of all patents, published applications and references cited herein are incorporated by reference in their entirety.

The present invention may be implemented in a variety of computer architectures. The PC 108 of FIG. 1 is for purposes of illustration and not a limitation of the present invention. The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

While this invention has been particularly shown and described with references to example embodiments thereof, it will be understood by those skilled in the art that various changes in form and details may be made therein without departing from the scope of the invention encompassed by the appended claims.

What is claimed is:

1. A method of simultaneously starting actions of devices connected to a host, the method comprising:
   transmitting successive start of frame signals to the connected devices, the start of frame signals being received by the connected devices at the same time;
   in the host:
   determining a starting frame number of a future frame at which actions of the devices are to start; and
   serially issuing start commands to the connected devices, each of the start commands being addressed to one of the connected devices and including the determined starting frame number; and
   in each of the connected devices:
   inspecting the received start of frame signals to determine associated frame numbers;
   receiving the start command addressed to the device and identifying the determined starting frame number; and
   upon receipt of a start of frame signal whose associated frame number is equal to the determined starting frame number, starting an action of the device.

2. The method as claimed in claim 1, wherein the connected devices are connected to the host via a USB connection.

3. The method as claimed in claim 1, wherein determining the starting frame number comprises determining the associated frame number of the start of frame signal as one that will be transmitted after all serially issued start commands have reached the connected devices.

4. The method as claimed in claim 1, wherein starting an action of the device comprises starting data acquisition with the connected devices.

5. An electronic device, the device being one of plural devices connected to a host, the device comprising electronics configured to:
   repeatedly receive a start of frame signal;
   inspect the received start of frame signal to determine an associated frame number;
   receive a start command issued by the host and addressed to the device, the start command being one of serially issued start commands by the host, each of the start commands being addressed to one of the connected devices and including a starting frame number of a future frame at which actions of the devices are to start, the starting frame number determined by the host; and
   upon receipt of a start of frame signal whose associated frame number is equal to the determined starting frame number, start an action of the device.

6. The electronic device as claimed in claim 5, wherein the host determines the starting frame number by determining the associated frame number of the start of frame signal as one that will be transmitted after all serially issued start commands have reached the connected devices.

7. The electronic device as claimed in claim 5, wherein the action of the device comprises data acquisition with the connected device.

8. The electronic device as claimed in claim 5, wherein the connected devices are connected to the host via a USB connection.

9. A system for simultaneously starting actions of devices, the system comprising:
   plural devices connected to a host, each of the devices comprising electronics configured to:
   repeatedly receive a start of frame signal, the start of frame signal being received by the connected devices at the same time;
   inspect the received start of frame signal to determine an associated frame number;
   receive a start command issued by the host and addressed to the device, the start command being one of serially issued start commands by the host, each of the start commands being addressed to one of the connected devices and including a starting frame number of a future frame at which an action of the devices is to start, the starting frame number determined by the host; and upon receipt of a start of frame signal whose associated frame number is equal to the determined starting frame number, start an action of the device.

10. The system as claimed in claim 9, wherein the host determines the starting frame number by determining the associated frame number of the start of frame signal as one that will be transmitted after all serially issued start commands have reached the connected devices.

11. The system as claimed in claim 9, wherein the action of the device includes data acquisition with the connected devices.

12. The system as claimed in claim 9, wherein the connected devices are connected to the host via a USB connection.

\* \* \* \* \*